United States Patent
Yamamura et al.

(10) Patent No.: US 9,249,445 B2
(45) Date of Patent: Feb. 2, 2016

(54) CELL DETECTION METHOD, AND MICROARRAY CHIP FOR USE IN THE METHOD

(75) Inventors: Shohei Yamamura, Takamatsu (JP); Shouki Yatsushiro, Takamatsu (JP); Masatoshi Kataoka, Takamatsu (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 747 days.

(21) Appl. No.: 13/060,531

(22) PCT Filed: Sep. 2, 2009

(86) PCT No.: PCT/JP2009/065370
§ 371 (c)(1),
(2), (4) Date: Apr. 14, 2011

(87) PCT Pub. No.: WO2010/027003
PCT Pub. Date: Mar. 11, 2010

(65) Prior Publication Data
US 2011/0189723 A1 Aug. 4, 2011

(30) Foreign Application Priority Data
Sep. 2, 2008 (JP) .................. 2008-225193

(51) Int. Cl.
*C12Q 1/04* (2006.01)
*G01N 33/50* (2006.01)
*G01N 33/569* (2006.01)

(52) U.S. Cl.
CPC .............. *C12Q 1/04* (2013.01); *G01N 33/5091* (2013.01); *G01N 33/56905* (2013.01)

(58) Field of Classification Search
CPC ........ C12Q 1/00; C12Q 2304/00; C12Q 1/04; C12M 1/00; C12M 1/34; C12N 11/00; C12N 11/01; G01N 33/5091; G01N 33/56905
USPC .......................................................... 435/29
See application file for complete search history.

(56) References Cited

U.S. PATENT DOCUMENTS

| | | | |
|---|---|---|---|
| 6,703,203 B2 | 3/2004 | Shao | |
| 6,998,236 B2 | 2/2006 | Shao | |
| 7,033,821 B2 * | 4/2006 | Kim et al. | 435/288.4 |
| 7,169,577 B2 * | 1/2007 | Wang et al. | 435/30 |
| 7,776,553 B2 * | 8/2010 | Love et al. | 435/7.1 |
| 2002/0048765 A1 | 4/2002 | Shao | |
| 2002/0187509 A1 | 12/2002 | Shao | |
| 2004/0197236 A1 | 10/2004 | Vanmaele et al. | |
| 2004/0238484 A1 | 12/2004 | Le Pioufle et al. | |
| 2006/0134704 A1 | 6/2006 | Muraguchi | |
| 2006/0199211 A1 | 9/2006 | Pohl et al. | |
| 2006/0227320 A1 | 10/2006 | Tamiya et al. | |
| 2007/0269794 A1 | 11/2007 | Ueda | |
| 2008/0014631 A1 | 1/2008 | Muraguchi et al. | |
| 2011/0195496 A1 | 8/2011 | Muraguchi et al. | |

FOREIGN PATENT DOCUMENTS

| | | |
|---|---|---|
| EP | 0751215 A2 | 1/1997 |
| EP | 1 780 262 A1 | 5/2007 |
| JP | H08163979 A | 6/1996 |
| JP | H09117277 A | 5/1997 |
| JP | 2002-338306 A | 11/2002 |
| JP | 2004-502929 A1 | 1/2004 |
| JP | 2004-125781 | 4/2004 |
| JP | 2004-144526 A1 | 5/2004 |
| JP | 2004-187676 A1 | 7/2004 |
| JP | 2004-536595 A | 12/2004 |
| JP | 2006-055157 A | 3/2006 |
| JP | 2006-61023 A1 | 3/2006 |
| JP | 2006-101708 A1 | 4/2006 |
| JP | 2006-181407 | 7/2006 |
| JP | 2008-82961 A | 4/2008 |
| JP | 2008-532045 A | 8/2008 |
| WO | WO 2004086010 A1 | 10/2004 |
| WO | 2005/069001 A1 | 7/2005 |

OTHER PUBLICATIONS

Rapid and Highly Sensitive Detection of Malaria-Infected Erythrocyts Using a Cell Microarray Chip PLOS ONE, vol. 5, No. 10, Jan. 1, 2010, E13179.
Supplementary European Search Report dated Dec. 14, 2011 for European Patent Application No. 09811528.0.
H. Gong, et al.; "Microfluidic handling of PCR solution and DNA amplification on a reaction chamber array biochip;" Biomed Microdevices; vol. 8; 2006; pp. 167-176 (10 Sheets)/Cited in International Search Report.
International Search Report for International Application No. PCT/JP2009/065370 dated Nov. 13, 2009.
Office Action dated Apr. 15, 2014 for corresponding JP patent application No. 2010-527805.

(Continued)

*Primary Examiner* — Robert Yamasaki
*Assistant Examiner* — Teresa E Knight
(74) *Attorney, Agent, or Firm* — Kratz, Quintos & Hanson, LLP

(57) ABSTRACT

Disclosed is a detection method for detecting a specific cell in a sample containing multiple cells including the specific cell. Specifically disclosed is a detection method for detecting a specific cell in a sample containing multiple cells including the specific cell, which comprises the following steps (1) and (2): (1) retaining cells contained in the sample on a microarray chip which comprises multiple microchambers, wherein each of the microchambers can contain multiple cells; and (2) confirming the presence or absence of the specific cell in the cells retained on the microarray chip.

15 Claims, 6 Drawing Sheets

(56) References Cited

OTHER PUBLICATIONS

Lab Chip, 2005, vol. 5, pp. 30-37; "Development of a microfabricated cytometry platform for characterization and sorting of individual leukocytes".
Anal. Chem., 2005, vol. 77, pp. 5628-5634; "Large-Scale Single-Cell Trapping and Imaging Using Microwell Arrays".
C. Anthony Poole et al., Keratocyte networks visualized in the living cornea using vital dyes, Journal of Cell Science, 1993, pp. 685-692, vol. 106.
Yoshinori Akamatsu, Water-repellent coating on glass, New Glass, 2006, pp. 27-34, vol. 21, with partial translation.

* cited by examiner

FIG. 10
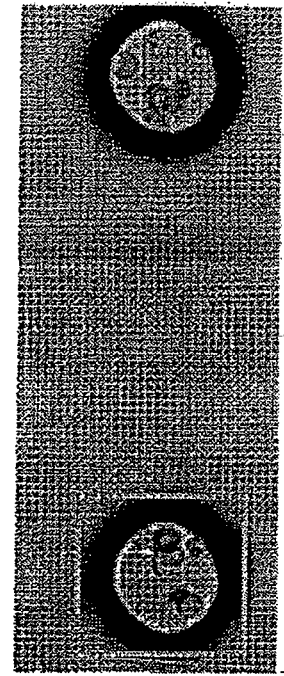
4-DAY CULTURE
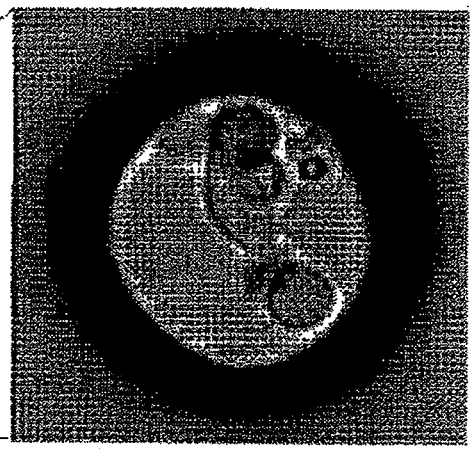
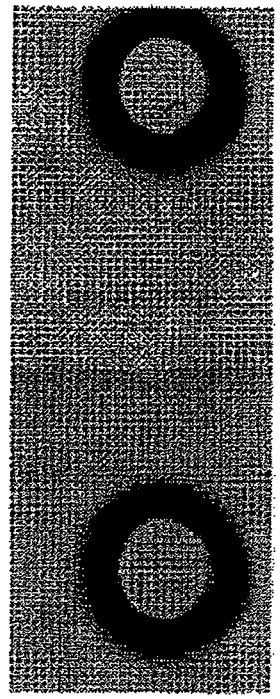
IMMEDIATELY AFTER INOCULATION

CELL DETECTION METHOD, AND MICROARRAY CHIP FOR USE IN THE METHOD

TECHNICAL FIELD

The present invention relates to a detection method for detecting a specific cell in a sample containing multiple cells. The invention also relates to a detection kit for detecting a specific cell in a sample containing multiple cells. The invention also relates to a microarray chip provided with multiple microchambers, and that can contain multiple cells in each microchamber. The invention also relates to a method for screening a drug candidate substance using a microarray chip provided with multiple microchambers.

BACKGROUND ART

Detection of only specific cells from a sample containing various types of cells is needed in a wide range of field. Particularly, in the biotechnological research and development and in the clinical practice associated with medicine and pharmacy, checking large numbers of cells for the presence or absence of specific cells (for example, cells containing or expressing a specific substance, cells infected with pathogens, and cancer cells) is very important for the progress of experiment and for disease diagnoses.

However, detection of specific cells from a sample containing large numbers of cells has been difficult, particularly when the percentage of the specific cells is low.

For example, in malaria parasite infection caused by the infection of red blood cells with malaria parasites, the following methods are available for the detection and diagnosis of the infection.

For example, in one method, blood cells are smeared on a glass slide, dried, and observed under a microscope after Giemsa staining to find the presence or absence of a malaria parasite infection or the extent of the infection. This method is advantageous, because it requires only the staining procedure for microscope observation, and is therefore easy to perform. The method, however, requires time and sophisticated observation techniques for the detection and diagnosis, and the detection sensitivity is very low. For example, the method takes as long as 40 minutes, and the detection sensitivity (detection limit) is only just high enough to detect infected cells accounting for at least about 0.01% of the whole blood cells.

In another method, the presence or absence of a malaria parasite infection or the extent of the infection is tested or diagnosed using immunochromatography. The method is widely known, and test kits are commercially available to enable easy testing. Such test kits offer even simpler procedures for observing the presence or absence of an infection or the extent of the infection. The immunochromatography takes only about 20 minutes; however, the detection sensitivity is only at the levels of microscope observation. Further, since the immunochromatography is prone to showing false positive results, it is common practice to combine the method with microscope observation.

Another method uses PCR to test and diagnose the presence or absence of a malaria parasite infection or the level of the infection. Unlike the microscope observation, the method offers high detection sensitivity. However, the PCR requires about 5 hours to produce results, and the procedure is complex and requires high skills. Further, depending on sample conditions and primers, setting reaction conditions is difficult, and detection may not be possible. The use of PCR alone is thus not suited for the diagnosis of infections.

Thus, in malaria parasite infection taken as an example above, the conventional detection and diagnosis methods have a number of drawbacks, including long hours, high skills, and poor detection sensitivity. Accordingly, there is a need for a novel infection detection method that is rapid, easy, and highly sensitive.

To date, various types of microarray chips have been reported, and used for various purposes, including cell detection. For example, Patent Literature 1 reports a system in which microchambers are integrated and connected to a heater and other parts of the system to enable high-throughput biochemical reactions of a biological sample. However, the system is not sensitive enough to enable detection at a single cell level, and high-sensitive detection of small numbers of target cells contained in large numbers of cells is difficult.

Patent Literature 2 reports a technique for observing the effect of a substance on cells. This is achieved by patterning a polymer on a substrate, and allowing cells to act on a substance of interest immobilized on the polymer. However, it is difficult with this technique to immobilize a certain number of cells on each pattern, and to detect small numbers of target cells in larger numbers of cells with high sensitivity.

Patent Literature 3 reports an array chip that includes large numbers of integrated microwells designed to contain a single lymphocyte per microwell. However, since only a single cell can be introduced to each microwell, screening of cells that outnumbers the microwells integrated on the array chip is difficult. Accordingly, it is difficult with this array chip to perform high-sensitive detection of small number of target cells contained in large numbers of cells (1 million to 10 million cells). It is also considered very difficult to culture the introduced cells or to perform PCR for these cells with the microwells of this array chip.

As described above, high-sensitive detection of small numbers of target cells (specific cells) contained in large number of cells is difficult to achieve with the conventional methods that use the microarray chips.

Under these circumstances, there is a need for a novel detection means that enables fast, easy, and high-sensitive detection of a variety of target cells (specific cells), including, for example, cells infected with various infections such as malaria parasite infection. There is also a need for a novel detection means that can easily be used, for example, at the bedside. However, no such detection means have been reported.

CITATION LIST

Patent Literature

PTL 1: JP-T-2004-502929
PTL 2: JP-A-2004-125781
PTL 3: JP-A-2004-187676

SUMMARY OF INVENTION

Technical Problem

An object of the present invention is to provide a method capable of detecting small numbers of target cells (specific cells) in large numbers of cells with high sensitivity. Another object of the invention is to provide a detection kit capable of detecting small numbers of target cells (specific cells) in large numbers of cells with high sensitivity. It is another object of the invention to provide a microarray chip capable of detecting small numbers of target cells (specific cells) in large numbers of cells with high sensitivity.

Solution to Problem

The present inventors conducted intensive studies over these backgrounds, and found that rapid, easy, and high-sensitive detection of the target specific cell is possible with the use of a microarray chip provided with multiple microchambers and capable of containing multiple cells in each microchamber. The present inventors also found that the number of cells contained in each microchamber of the microarray chip can be controlled by varying, for example, the size of the microchambers, so that only an arbitrarily-decided, certain number of cells can be contained in each microchamber. The present inventors also found that rapid, easy, and high-sensitive detection of target cells is possible with the use of a microarray chip provided with multiple microchambers, capable of containing multiple cells in each microchamber, and having a surface water contact angle of 10° or less, because such microarray chips enable a certain number of target cells to be evenly contained in each microchamber, and large numbers of target cells to be retained in a single microarray chip. The present invention has been completed based on these findings upon further studies, and includes, for example, the following items.

Detection Method
Item 1
A method for detecting a specific cell in a sample containing multiple cells,
the method comprising the steps of:
(1) retaining sample cells in a microarray chip provided with multiple microchambers and capable of containing multiple cells in each microchamber; and
(2) confirming the presence or absence of the specific cell in the cells retained in the microarray chip.
Item 2
A detection method according to Item 1, wherein the microchambers have an inner diameter-to-depth ratio of 1:0.35 to 1.
Item 3
A detection method according to Item 2, wherein the microchambers have an inner diameter of from 20 to 500 μm, and a depth of 20 μm or more.
Item 4
A detection method according to any one of Items 1 to 3, wherein the specific cell is a cell infected with an infection causative, agent.
Item 5
A detection method according to Item 4, wherein the infection causative agent is a malaria parasite.
Item 6
A detection method according to any one of Items 1 to 5, wherein the sample containing multiple cells is a sample containing multiple blood cells.
Item 7
A detection method according to any one of Items 1 to 6, wherein the microarray chip is capable of containing at least 10 cells per microchamber.
Item 8
A detection method according to any one of Items 1 to 7, wherein the microarray chip includes at least 1,000 microchambers.
Item 9
A detection method according to any one of Items 1 to 8, wherein the microarray chip has a surface that has a water contact angle of 10° or less.

Detection Kit
Item 10
A detection kit for detecting a specific cell in a sample containing multiple cells,
the detection kit including a microarray chip provided with multiple microchambers, and that is capable of containing multiple cells in each microchamber.
Item 11
A detection kit according to Item 10, wherein the sample containing multiple cells is a sample containing multiple blood cells, and wherein the specific cell is a blood cell infected with an infection causative agent.

Microarray Chip
Item 12
A microarray chip that includes multiple microchambers, wherein the microarray chip is capable of containing multiple cells in each microchamber, and has a surface that has a water contact angle of 10° or less.
Item 13
A microarray chip according to Item 12, wherein the microchambers have an inner diameter-to-depth ratio of 1:0.35 to 1.
Item 14
A microarray chip according to Item 13, wherein the microchambers have an inner diameter of from 20 to 500 μm, and a depth of 20 μm or more.
Item 15
A microarray chip according to any one of Items 12 to 14, wherein the microchambers are disposed in a grid, and the shortest distance between the microchambers is 10 to 300 μm.
Item 16
A microarray chip according to any one of Items 12 to 15, wherein cells are retained in the microchambers.

Drug Candidate Substance Screening Method
Item 17
A method for screening a drug candidate substance using a microarray chip provided with multiple microchambers and that retains cells in the microchambers,
the method including the steps of:
(1) adding a drug candidate substance to the microchambers retaining the cells; and
(2) measuring the effect of the drug candidate substance on the cells, and selecting a substance exhibiting a desired activity.
Item 18
A screening method according to Item 17, further including culturing the cells in the microchambers after the step (1), and applying the cultured cells to the step (2).
Item 19
A screening method according to Item 17 or 18, wherein the microchambers have an inner diameter-to-depth ratio of 1:0.35 to 1.
Item 20
A screening method according to Item 19, wherein the microchambers have an inner diameter of from 20 to 500 μm, and a depth of 20 μm or more.

Advantageous Effects of Invention

Detection Method
The detection method of the present invention enables more rapid, easier, and more sensitive detection of a specific cell in a sample containing multiple cells than conventional detection methods.

Detection Kit

The detection kit of the present invention enables more rapid, easier, and more sensitive detection of the target specific cell in a sample containing multiple cells.

Microarray Chip

The microarray chip of the present invention enables more rapid, easier, and more sensitive detection of the target specific cell in a sample containing multiple cells.

Drug Candidate Substance Screening Method

The drug candidate substance screening method of the present invention can easily and rapidly measure the effects of various drug candidate substances on cells, and can efficiently select a substance exhibiting a desired activity.

Description of Embodiments (a) Detection Method

A detection method of the present invention is described below.

In the detection method of the present invention, large numbers of cells are retained in a microarray chip, and the detection target specific cell is detected from these cells. For example, as many as 1 million cells can be retained in a single microarray chip, and the specific cell can be detected even when these large numbers of cells contains only one target specific cell. In this case, the detection method of the present invention can be said as being capable of detecting a specific cell that accounts for only 0.0001% of all the cells in a sample.

In the detection method of the present invention, the detection target specific cell, and the large numbers of cells containing the specific cell (namely, a cell group) are not particularly limited.

For example, a cell expressing a specific gene, or a cell containing excess levels of biological substances such as nucleic acids, proteins, lipids, and sugars, or deficient in these substances can be detected as a specific cell from a variety of cell groups. The specific cell may be a cell found in nature, or a cell subjected to artificial treatments. The natural cells are not particularly limited, and may be, for example, pathogenic cells, diseased cells, cells infected with pathogens or pathogenic organisms, mutated cells, and unknown cells of specific properties. The artificial treatments are not particularly limited, and may be, for example, physical treatments (e.g., irradiation of electromagnetic wave), chemical treatments (e.g., drug treatment), or genetic engineering processes (e.g., gene recombinant process).

A cell group may be subjected to an artificial treatment that has known effects on cells, and an unaffected cell or a strongly affected cell may be detected as a specific cell. For example, a cell that shows resistance or high sensitivity to a drug treatment may be detected as a specific cell.

The cell group is not limited either, and may be a group of unicellular organisms, or a group of multicellular organism-derived cells. Examples of multicellular organism-derived cells include cells obtained from a normal tissue or a diseased tissue of an organism, and cultured cells derived from such cells. The source organism of these cells is not limited. For example, the cells may originate in animals or plants. More specific examples include, but are not limited to, vertebrates (mammals and birds in particular), insects, and plant cultures. Further, the cell group may be a group of the same cells or different cells.

Specifically, the detection method of the present invention can be used to detect, for example, a malaria parasite-infected red blood cell from the blood cells of a malaria parasite-infected patient. The infected blood cell in a malaria parasite infection can be detected even when only one out of as many as about 1 million blood cells is infected. Further, the method also can be preferably used, for example, in search of a cancer stem cell present in a cancer cell group. Further, for example, a cell that has acquired a specific property as a result of an artificial treatment can be selected from a cell group subjected to the artificial treatment. Further, a cell that exhibits a particularly strong specific property also can be selected. More specifically, for example, a cell producing a specific substance with particularly high efficiency can be detected from multiple cells transformed to produce the specific substance after a gene recombinant process. Alternatively, for example, a cell that has lost a specific function after irradiation with electromagnetic waves or after a drug treatment may be detected. A cell that has resistance or high sensitivity to these processes also can be detected.

The detection method of the present invention is capable of rapid, easy, and high-sensitive detection of a specific cell, for example, such as above, and thus can be suitably used not only in laboratories but also in, for example, the clinic.

In laboratories, the detection method can be used, for example, for the detection (and thus screening) of cells having specific properties (for example, such as drug resistance, drug sensitivity, expression of a specific genes, and excess or deficient levels of specific biological substance), and for further analysis of the detected cells. The post-detection analysis of the specific cell is not particularly limited, and may be, for example, staining or fluorescence staining, PCR analysis, or culturing in the microchambers. Further, the cells may be collected from the microchambers, and cultured for further analyses.

In the clinic, the detection method can suitably be used, for example, for disease diagnoses (cytodiagnosis in particular). For example, a pathogenic cell, a diseased cell, or a cell infected with pathogens or pathogenic organisms can be detected in a cell group of a tissue collected from a suspected human individual, and the detection result can be used for diagnosis. Further, the detected cells can be tested for drug resistance or sensitivity, or subjected to gene analysis by PCR or FISH, inside the microchambers. Further, the cells may be cultured inside or outside the microchambers to further study the property of the cells. More specifically, for example, the presence or absence of infected cells can be quickly grasped alongside a patient with possible infection, for example, at the bedside. Further, using a surgically collected cancer (for example, blood cancer) tissue, the proportion of cancer cells with resistance or sensitivity to an anticancer agent can be assessed, and used for therapy.

Further, in the detection method of the present invention, the target specific cell in multiple cells (a cell group) contained (retained) in each microchamber of the microarray chip may be labeled so as to be specifically detected. Further, the target specific cell may be labeled in advance in a multiple cell (cell group) -containing sample. Of these labeling methods, it is more preferable to label the specific cell in advance, because it can provide more uniform labeling efficiency. The labeling method is not particularly limited, and may be appropriately selected according to the property of the target specific cell. However, fluorescence labeling is preferred considering factors such as the ease of detection and toxicity. The specific cell can be detected based on the presence or absence of a label (for example, a fluorescence label). Further, the cells may be analyzed quantitatively to find the proportion of specific cells in sample cells, based on the number of detected labels (for example, fluorescence labels). Further, the property intensity of the detected specific cell can be analyzed based on the intensity of the label (for example, the fluorescence intensity of the fluorescence label). Specifically, for example, when the target specific cell is a cell infected with an infection causal agent, the seriousness or stage of the infection can be analyzed by looking at the quantitative data or the label intensity of individual cells (for example, the fluorescence intensity in the case of a fluorescence label). Further, when the target specific cell is a cell that has acquired a specific property after an artificial treatment, the percentage of the cells that can acquire the specific property from the specific artificial treatment, or the expression strength of the property in each cell can be determined. This provides ways to study the extent of the efficiency of a particular artificial treatment changing the property of the cells, or how the property is changed.

In the detection method of the present application, the cells are contained in the microchambers of the microarray chip. Thus, in the detection method of the present application, the target specific cell in the microarray chip can easily be spotted during the detection. This makes it easier, for example, to collect the specific cell, or to perform a further analysis by PCR after the detection.

Further, in the detection method of the present application, the cells can be evenly and efficiently contained in each microchamber of the microarray chip. Specifically, in the detection method of the present application, each microchamber of the microarray chip can contain about the same number of cells.

Note that the cells can be evenly retained as a single layer (monolayer) of cells at the bottom of the microchambers, when the microchambers have an inner diameter-to-depth ratio of, for example, 1:0.35 to 1, though the ratio is not limited to this. Specifically, the cells can be retained with almost no overlap at the bottom of each microchamber. Thus, detection problems caused when the target specific cell is underneath the overlying cells in the microchamber are unlikely to occur. Further, because the cells form a monolayer, a focal point can easily be set in microscopy. Confocal laser microscope observation is also possible with high sensitivity, because of the suppressed background.

Though not limited, the microarray chip used in the detection method of the present invention is preferably the microarray chip of the present invention described later.

The multiple cell-containing sample used for the detection method of the present invention is not particularly limited, as long as it possibly contains a cell group that includes the target specific cell. Specific, non-limiting examples of the cell group and the target specific cell are described below.

(a)-1. Examples of Target Specific Cells
(a)-1-1. Infected Blood Cells in Infection An infected blood cell in an infection can be detected by using the detection method of the present invention. Examples of infection include protozoal infections represented by malaria parasite infection, viral infections represented by human immunodeficiency virus (HIV) infection, and bacterial infections represented by *Mycobacterium tuberculosis* infection.

For example, in infections caused by malaria parasites, malaria parasites infect red blood cells. In this case, the specific cell as the detection target of the detection method of the present invention is the blood cell infected with malaria parasites, specifically, the red blood cell infected with malaria parasites. For example, there are four kinds of malaria parasites: tropical malaria parasite, tertian malaria parasite, quartan malaria parasite, and ovale malaria parasite.

In HIV infection, for example, the HIV infects certain lymphocytes (T cells). In this case, the specific cell as the detection target of the detection method of the present invention is the HIV-infected blood cell, specifically, certain lymphocytes (T cells) infected with HIV. The HIV may be HIV-1 or HIV-2, for example.

In tuberculosis, for example, *Mycobacterium tuberculosis* infects certain white blood cells (monocytes). In this case, the specific cell as the detection target of the detection method of the present invention is the blood cell infected with *Mycobacterium tuberculosis*, specifically, certain white blood cells (monocytes) infected with *Mycobacterium tuberculosis*.

The detection method of the present invention is also applicable for the detection of other infected blood cells in other infections.

The blood cell is not limited, as long as it is a cell contained in the blood. Examples of blood cell include red blood cells, blood platelet, and white blood cells (lymphocytes, monocytes, neutrophils, eosinophils, basophils). For example, a sample containing these blood cells can be used as a multiple-cell containing sample in the detection method of the present invention. For example, the blood or bodily fluid containing multiple blood cells can be used as the sample.

(a)-1-2. Marker Expressing Cell in Cultured Cells

A specific cell in a cultured cell can be detected by using the detection method of the present invention. The cultured cells are not particularly limited, and, for example, mammal- or insect-derived cell lines (for example, HEK293 cells, Hela cells, 3T3 cells, COS-7 cells, CHO cells, Jurkat cells, and Sf9 cells), and yeasts can be preferably used.

The detection method of the present invention can sufficiently detect the specific cell even when the sample contains only a very small number of target specific cells (for example, the percentage of specific cells as low as 0.0001% in a sample). Thus, the detection method is particularly advantageous for samples that contain a very small percentage of target specific cells. An example of such samples is a cancer cell group that contains cancer stem cells. The cancer stem cells, capable of self replication and proliferation, are present in only small numbers in a malignant tumor (cancer), and are believed to express markers (for example, CD34, CD133, CD117, Sca-1) as do the stem cells. The cancer stem cells are therefore considered to be preferable for the detection by the detection method of the present invention.

Cells expressing specific genes or proteins are also the targets of the detection by the detection method of the present invention.

(a)-2. Microarray Chip

The microarray chip used in the detection method of the present invention is not limited, as long as it includes multiple microchambers, and can contain multiple cells in each microchamber.

The substrate of the microarray chip is not limited. Examples include polymers such as polystyrene, polyethylene, polypropylene, polyamide, polycarbonate, polydimethylsiloxane (PDMS), polymethylmethacrylate (PMMA), and cyclic olefin copolymers (COC); metals such as silicon; glass; fused quartz; and composites of different materials, such as a polymer joined to glass or a metal (for example, a PDMS-glass composite). The preferred materials include polystyrene, PMMA, glass, and silicon.

The size of the microarray chip is not limited, and is appropriately selected according to the type of the device used to detect and measure the target specific cell.

The microarray chip includes microchambers. The microchambers may be fabricated by directly processing the substrate, or by attaching a microhole- or microchamber-formed film to the substrate. Preferably, the microchambers are fabricated by directly processing the substrate. In this case, the microchambers may be fabricated using microfabrication lithography techniques, such as photolithography and electron lithography, used in semiconductor researches, or any other techniques used to form microholes, including drilling with a microdrill, and a laser process. An example of such processes is a LIGA (Lithographie Galvanoformung Abformung) process.

The microarray chip may be subjected to a surface treatment, as required. The surface treatment method is not limited, and may be performed by, for example, a plasma process, or a corona discharge process. Preferably, the surface treatment is performed by a plasma process such as an oxygen plasma process. For example, when the substrate of the microarray chip is a hydrophobic material (for example, a polymer such as polystyrene and PMMA), it is preferable to perform a hydrophilic treatment such as an oxygen plasma process. Such processes are not necessary when the substrate of the microarray chip is a hydrophilic material (such as silicon and glass). The microarray chip may be conditioned by further surface treatment such as coating with proteins or lipids.

The shape of the microchambers is not particularly limited. Examples of microchamber shape include a cylinder, an inverted hemisphere, an inverted cone, an inverted pyramid (an inverted triangular pyramid, an inverted quadrangular pyramid, an inverted pentagonal pyramid, an inverted hexagonal pyramid, heptagon and higher inverted geometrical pyramids), a cuboid, and combinations of two or more of these shapes. The bottom of the cylinders and cuboids is usually flat, but may be curved, or convex or concave. In the case of an inverted cone or inverted pyramid, the bottom surface becomes the microchamber opening; however, the apex of the inverted cone or inverted pyramid may be truncated (to make the bottom of the microchamber flat). The bottom of the microchamber formed as a truncated inverted cone or a truncated inverted pyramid may have a non-flat surface, such as a curved surface, as above. The preferred shape of the microchamber is a cylinder, an inverted hemisphere, an inverted cone, or an inverted pyramid, of which the cylinder and the inverted hemisphere are more preferred, and the cylinder is most preferred. Preferably, the microchambers all have the same shape in a single microarray chip.

The number of cells contained in the microchambers is appropriately decided according to such factors as the concentration of all cells contained in a sample, the percentage of the target specific cells in all cells contained in a sample, and the dimensions and the number of the microchambers (described later). The detection sensitivity for the target specific cell can be increased by increasing the number of cells retained in the microarray chip.

From this standpoint, it is preferable to retain as many cells as possible in a single microarray chip. Retaining cells in the microarray chip means containing the cells in the microchambers of the microarray chip. Accordingly, the number of cells retained in the microarray chip can be increased by increasing the number of microchambers, or by increasing the number of cells that can be contained in each microchamber.

Preferably, at least 10,000 cells are retained in a single microarray chip, though the number is not particularly limited. The number of cells retained in a single microarray chip is more preferably at least 100,000, further preferably at least 1 million, and even more preferably at least 10 million.

For example, when detecting the target cell that may be present 1 in 1 million cells, it is preferable to retain at least 1 million cells in a single microarray chip. More preferably, 2 million to 10 million, further preferably 3 million to 10 million cells should be supported. In this case, it is particularly preferable to provide at least 10,000 microchambers in a single microarray chip.

The number of cells contained in each microchamber is not limited, as long as the microarray chip can retain cells, and each microchamber can contain at least two cells. From the standpoint that the detection sensitivity for the target specific cell can be increased by increasing the number of cells retained in the microarray chip, it is preferable, as above, to contain at least 10 cells, preferably 50 to 500 cells, further preferably 100 to 300 cells in each microchamber.

For example, a single microarray chip retains about 1 million cells, when the microarray chip includes 100,000 microchambers, and when each microchamber contains about 10 cells.

The dimensions of each microchamber are not limited, as long as each microchamber can contain cells. Preferably, the microchambers are so dimensioned as to contain about the same number of cells in each microchamber. It is therefore preferable that all microchambers have the same dimensions. Note that when the opening of the microchamber is circular, the "inner diameter" refers to the diameter of the opening of each microchamber on the microarray chip surface. When the opening of the microchamber is not circular, the "inner diameter" refers to the length of a side of the microchamber opening. The term "depth" is used to refer to the distance from the microchamber opening to the deepest portion of the microchamber.

Preferably, the inner diameter and depth of the microchambers have a certain ratio. Specifically, the inner diameter-to-depth ratio is preferably 1:0.35 to 1, more preferably 1:0.35 to 0.85, further preferably 1:0.4 to 0.85, and even more preferably 1:0.45 to 0.8.

The inner diameter of the microchambers is preferably 20 to 500 µm, more preferably 20 to 400 µm, further preferably 20 to 300 µm, even more preferably 30 to 250 µm, particularly preferably 30 to 200 µm. The depth, which depends on the inner diameter, is preferably 20 to 200 µm, more preferably 20 to 100 µm, further preferably 20 to 80 µm, even more preferably 20 to 70 µm, particularly preferably 30 to 70 µm.

The preferred depth of the microchambers can be determined once the inner diameter is decided from the preferred inner diameter-to-depth ratio. It should be noted, however, that the microchambers should preferably have a depth of 20 µm or more to contain cells. Taken together, it is particularly preferable that the microchambers have the foregoing ranges of inner diameter-to-depth ratio, the foregoing ranges of inner diameter, and a depth of 20 µm or more.

With these dimensions, the microchambers can evenly and efficiently contain cells in the form of a monolayer.

The number of microchambers is not particularly limited either. The detection sensitivity for the infected blood cell increases with increase in the number of cells retained in the microarray chip, as described above. From this standpoint, the number of microchambers per microarray chip is at least 1,000, more preferably 2,000 to 50,000, further preferably 2,000 to 20,000.

The distance between the microchambers is not particularly limited. As illustrated in FIG. 1, when the microchambers are disposed in a grid, the shortest distance between the microchambers, specifically, the distance (i) in FIG. 1, is, for example, 10 to 300 µm, preferably 50 to 300 µm, more preferably 100 to 200 µm.

For example, the distance (i) may be 100 to 200 µm when the number of contained cells per microchamber is about 100, and when each microchamber has an inner diameter of 100 µm, and a depth of 50 to 100 µm.

The parameters of the microchambers, including shape, number, dimensions, and the distance between the microchambers are appropriately decided by skilled artisan according to such factors as the percentage of the target specific cells in all cells in a sample, the number of cells to be contained in the microchambers, and the number of cells to be retained in the microarray chip.

The surface conditions of the microarray chip are not limited, as long as the cells can be retained on the microarray chip. The surface of the microarray chip is preferably hydrophilic, depending on the type of cells retained in the microarray chip. Specifically, the cells can be contained more efficiently, and about the same number of cells can be evenly contained in the form of a monolayer in each microchamber when the water contact angle on the surface of the microarray chip is preferably 10° or less. From this standpoint, the water contact angle on the surface of the microarray chip is more preferably 8° or less, further preferably 5° or less. Note that the "surface of the microarray chip" is meant to also include the inner surface of the microchambers.

Thus, the substrate surface of the microarray chip does not require a further treatment when the water contact angle on the substrate surface falls within the foregoing preferable ranges. If the water contact angle falls outside of the foregoing ranges, the surface may be treated to provide a preferable water contact angle. A skilled artisan would be able to choose and perform a surface treatment that optimizes the water contact angle of the microarray chip, taking into account the extent of cell adhesion. For example, when a polymer material is used for the substrate of the microarray chip, the surface may be treated with, for example, oxygen plasma to adjust the water contact angle.

Note that the water contact angle is measured as follows. The water contact angle is measured by using the known $\theta/2$ method. The $\theta/2$ method is a method that finds the contact angle from the angle between a solid surface and the line that joins the apex and the end points on the left and right of a liquid droplet. For example, in order to determine the surface water contact angle of the microarray chip, distilled water is dropped at different surface points, and the contact angle of each droplet is determined. The value obtained from this contact angle can then be used as the water contact angle. For example, the water contact angle may be measured by dropping 1 to 2 µl of distilled water at different points (at least 5 points) on a microarray chip surface according to this method, using a contact angle meter (Kyowa Interface Science Co., Ltd.).

For example, a microarray chip is formed that includes a grid of cylindrical microchambers distant apart by a distance (i) of 100 to 200 µm, and that has a surface water contact angle of 10° or less. Each microchamber is dimensioned to have an inner diameter of 100 µm, and a depth of 50 to 100 µm, so as to contain about 100 cells per microchamber. With such a microarray chip, the cells can be more evenly and efficiently contained as a monolayer in each microchamber.

(a)-3. Microarray Chip Fabrication Method

The microarray chip is appropriately fabricated using methods known in the art. For example, the microarray chip may be fabricated by being molded out of a chip template fabricated by using lithography and etching techniques. In the present invention, the microarray chip is fabricated by this method. Specifically, the microarray chip may be fabricated from a polymer (plastic) material used as the microarray chip substrate, according to the LIGA process using X-ray lithography (electron lithography) and electroforming (plating) techniques.

(a)-4. Steps in the Detection Method of the Present Invention

The detection method of the present invention is a method for detecting a specific cell contained in a sample containing multiple cells, and includes at least the steps of:

(1) retaining sample cells in a microarray chip provided with multiple microchambers and capable of containing multiple cells in each microchamber; and (2) confirming the presence or absence of the specific cell in the cells retained in the microarray chip.

The cells are retained in the microarray chip at least after the procedures that include contacting the cells to the microarray chip and developing the cells on the microarray chip to contain the cells in each microchamber, and removing (washing) the excess cells from the microarray chip.

The method of contacting the cells to the microarray chip is not limited, as long as the cells are brought into contact with the microarray chip.

For example, the cultured cells or collected cells from an organism may be contacted with the microarray chip either by themselves or as a mixture after being mixed with a solution such as a buffer or a culture solution.

For example, the blood cells may be contacted to the microarray chip by contacting (e.g., adding or dropping) the collected blood itself to the microarray chip, or as a mixture with a solution such as a buffer and a culture solution. Further, the blood cells may be contacted to the microarray chip as a mixture obtained by separating blood cells from the collected blood and mixing the separated blood cells with a solution such as a buffer and a culture solution.

Further, cultured cells (for example, mammal- or insect-derived cells, and yeasts) may be contacted with the microarray chip by contacting (for example, adding or dropping) the cultured cells either directly with the medium, or as a mixture of the cultured cell-containing medium with a solution such as a buffer and a culture solution. Further, the cultured cells collected from the medium may be contacted with the microarray chip after being mixed with a solution such as a buffer and a culture solution.

The method of developing the cells on the microarray chip is not limited, as long as the cells can be developed on the microarray chip. The cells may be developed on the microarray chip by contacting the multiple cells (a cell group) themselves to the microarray chip, or may be developed with a developing solution after being contacted. Examples of developer include a buffer, a culture solution, and a surfactant.

For example, when the cells developed on the microarray chip are blood cells, the blood cells may be developed on the microarray chip by being contacted to the microarray chip in the manner described above, or the contacted blood cells may be developed with a developer. Further, for example, when the developed cells are cultured cells, the cultured cells can be developed on the microarray chip in the same manner as with the case of the blood cells. The cells (for example, blood cells, cultured cells) can be contained in each microchamber at least after these procedures. When it is difficult to develop the cells on the chip (particularly, as in the case where air remains at the bottom of the chambers), the cells may be contacted and developed on the microarray chip after developing a solution to prevent entry of air in the microchambers, for example, by performing sonication beforehand for the chip placed in a solution such as a medium and a buffer, or by rubbing the chip surface with a brush or the like.

The concentration of the developed cells on the microarray chip is not particularly limited, and may be, for example, $1 \times 10^{10}$ to $1 \times 10^4$ (cells/ml), depending on the cell type. The cells can be contained substantially evenly as a monolayer in each microchamber by removing the excess cells after the development. The concentration of the developed cells may be appropriately adjusted according to the type of cells and microarray chip used.

The method of removing (washing) the excess cells from the microarray chip is not limited, as long as the excess cells can be removed from the microarray chip (specifically, from the inside and outside of the microchambers).

For example, the excess cells may be removed by flowing a washing solution such as a buffer, a culture solution, a surfactant, and an enzyme along a slightly tilted surface of the microarray chip, using a Pipetman or the like. Further, an instrument such as a cell scraper may be used for the removal and washing of the excess cells adsorbed on regions other than the microchambers.

Note that the number of cells contained in each microchamber after the removal procedure can be reduced when concentration of the developed cells is low (for example, a red blood cell concentration of $1\times10^6$ cells/ml or less) than when the concentration of the developed cells is high (for example, a red blood cell concentration of $1\times10^8$ cells/ml or more). In either case, about the same number of cells is contained in each microchamber. Thus, the number of cells evenly contained as a monolayer in each microchamber can be adjusted to one to several cells by setting a lower concentration for the developed cells. Increasing the concentration of the developed cells does not increase the number of cells contained in the microchambers, because the cells after the removal procedure are evenly contained in the microchambers as a monolayer. The number of cells that can be contained is limited by the bottom surface area of the microchambers.

The removal (washing) of the excess cells from the microarray chip is performed preferably after the cells have properly adsorbed on the microchambers following the contact and development of the cells on the microarray chip. The adsorption time is not limited, and may be appropriately adjusted by a skilled artisan.

The method of confirming the presence or absence of the target specific cell is not limited, as long as the specific cell can be detected.

For example, when the target specific cell is a cell that shows a morphological change, the cell can be detected by observing the morphology of the cell with a microscope. Further, when a substance that specifically binds to the specific cell is present, the cell can be detected by confirming the presence or absence of such binding using such a substance. Non-limiting examples of such substances include antibodies and aptamers. Further, when a substance that specifically reacts with the specific cell is present, the cell can be detected by confirming the presence or absence of a reaction using such a substance.

The method of confirming the presence or absence of such binding and reactions is not particularly limited, and fluorescence can preferably be used. For example, when the substance that specifically binds to the specific cell is fluorescence-labeled, only the specific cell in a sample can be labeled. The presence or absence of the specific cell can then be confirmed by the presence or absence of fluorescence.

Specifically, the presence or absence of the specific cell can be confirmed by first conjugating fluorescence labels in a manner allowing only the specific cell in a sample to be labeled, prior to contacting the sample to the microarray chip, and then detecting the fluorescence labels after the cells are retained in the microchambers. Further, only the specific cell may be fluorescence-labeled after the cells are retained in the microchambers.

For example, when detecting a pathogenic microorganism-infected blood cell from blood cells, the nucleus of the pathogenic microorganism in the infected blood cell is fluorescence-stained before contacting the blood cells to the microarray chip, and the infected blood cell is detected based on the fluorescence using a device such as a fluorescence microscope and an array scanner. Alternatively, the infected blood cell also can be detected by fluorescence-staining the nucleus of the pathogenic microorganism in the blood cell in the same manner, after the blood cells are contained in the microchambers formed in the microarray chip. For example, when detecting the infected blood cell at the bedside, the infected blood cell can be detected more easily when the nucleus or other parts of the pathogenic microorganism in the infected blood cell is fluorescence-stained before contacting and developing the blood cells on the microarray chip, because it makes the post-processes of the contact and development easier. Further, for example, the target is not limited to the nucleus of the pathogenic microorganism in the blood cell, and, for example, fluorescence-labeled antibodies may be used to target a specific protein (specific amino acid sequence), or fluorescence-labeled probes may be used to target a specific gene sequence.

Further, for example, when detecting a cell expressing a specific marker in cultured cells, fluorescence-labeled antibodies specific to the marker are allowed to act on the cultured cells in advance, and the specific cell can be detected based on the fluorescence using a device such as a fluorescence microscope and an array scanner, after the cells are retained in the microchambers. Alternatively, the fluorescence-based detection may be performed by labeling the specific marker-expressing cell in cultured cells with fluorescence-labeled antibodies after the cultured cells are contained in the microchambers formed in the microarray chip.

As a specific example, the infected red blood cell is labeled by the fluorescence-staining of the nucleus of an infectious microorganism such as a protozoan in a suspension of red blood cells containing the infected red blood cell. In some cases, the red blood cells are also labeled with, for example, a fluorescence substance. The suspension of the red blood cells containing the labeled infected red blood cell is then developed on the microarray chip, and, after removing and washing the excess blood cells, the target cell is fluorescence detected with a device such as a fluorescence microscope and a microarray scanner. In this way, in addition to finding the presence or absence of an infection, other information such as the stage and the type of infection also can be analyzed by examining, for example, the fluorescence intensity and the number of labeled cells.

In the detection method of the present invention, for example, as illustrated in FIG. 2, 50×200 microchambers may be disposed along the columns and rows of the microarray chip, and each microchamber may contain 100 blood cells. The infection rate can be determined to be 1%, when the number of infected blood cells after the detection is 1 per microchamber.

Further, in the detection method of the present invention, the infected blood cell can be detected even when, for example, only one out of a total of 1 million blood cells retained in the microarray chip is infected. In this case, the detection method of the present invention can be said as being capable of detecting an infected blood cell that accounts for only 0.0001% of all the blood cells in a sample.

(b) Detection Kit

The detection kit of the present invention is a kit for detecting a specific cell in a sample containing multiple cells. The detection kit includes a microarray chip provided with multiple microchambers and capable of containing multiple cells in each microchamber.

The detection kit can detect the target specific cell in a sample containing multiple cells, more rapid, more easily, and with higher sensitivity. For example, the presence or absence of an infected blood cell in an infection, or the extent of infection can be detected both rapidly and easily with high sensitivity. Alternatively, for example, a cancer stem cell in a cancer cell group can be quickly detected. It is also possible, for example, to screen for a specific gene-expressing cell in a cell group that contains a cell expressing a specific gene (for example, a group of cultured cells or yeasts).

(b)-1. Target Specific Cell

The target specific cell of the detection by the detection kit of the present invention is as described above.

(b)-2. Microarray Chip Contained in Detection Kit

The microarray chip contained in the detection kit of the present invention is as described above.

(b)-3. Fabrication Method of Microarray Chip Contained in Detection Kit

The fabrication method of the microarray chip contained in the detection kit of the present invention is as described above.

(b)-4. Additional Components of Detection Kit Other than Microarray Chip

The detection kit of the present invention may additionally include components other than the microarray chip. Non-limiting examples of such additional components include the following.

The detection kit of the present invention may further include a buffer or a culture solution used to contact cells to the microarray chip.

The detection kit of the present invention may further include a buffer, a culture solution, or a surfactant used to develop cells on the microarray chip.

The detection kit of the present invention may further include a washing solution such as a buffer, a culture solution, a surfactant, and an enzyme used to remove (wash) the excess cells from the microarray chip.

The detection kit of the present invention may further include a Pipetman or the like used to contact and develop cells on the microarray chip, and to remove the cells from the microarray chip.

The detection kit of the present invention may further include an instrument, such as a cell scraper, used to remove and wash the excess cells adsorbed on regions other than the microchambers.

The detection kit of the present invention may further include a device for detecting the target specific cell. Examples of such devices include a fluorescence microscope, and a microarray scanner.

Further, for example, when the target specific cell is detected by fluorescence staining in the end, the detection kit of the present invention may further include a fluorescence staining agent for staining the specific cell (for example, a fluorescence dye, fluorescence-labeled antibody).

The detection kit of the present invention may further include a user's manual for the detection kit.

With the use of the detection kit of the present invention, the target specific cell can be detected both rapidly and easily, even when the percentage of the specific cell in a sample is low (for example, 0.0001%).

(c) Microarray Chip

The microarray chip of the present invention is described below.

The microarray chip of the present invention can be described as above, so long as the microarray chip at least includes multiple microchambers, and can contain multiple cells in each microchamber, and has a surface that has a water contact angle of 10° or less.

Configured this way, the microarray chip of the present invention can evenly contain a certain number of cells in each microchamber. From the standpoint of more efficiently containing a certain number of cells evenly in each microchamber, the water contact angle of the microarray chip is preferably 10° or less, more preferably 8° or less, further preferably 5° or less. Note that the water contact angle can be adjusted in the manner described above.

Similarly, from the standpoint of more efficiently containing a certain number of cells evenly in each microchamber, it is preferable that the inner diameter and depth of the microchambers have a certain ratio, specifically, the inner diameter-to-depth ratio of preferably 1:0.35 to 1, more preferably 1:0.35 to 0.85, further preferably 1:0.4 to 0.85, and even more preferably 1:0.45 to 0.8.

The inner diameter of the microchamber is preferably 20 to 500 μm, more preferably 20 to 400 μm, further preferably 20 to 300 μm, even more preferably 30 to 250 μm, and particularly preferably 30 to 200 μm. The depth, which depends on the value of inner diameter, is preferably 20 to 200 μm, more preferably 20 to 100 μm, further preferably 20 to 80 μm, even more preferably 20 to 70 μm, particularly preferably 30 to 70 μm.

The preferred depth of the microchambers can be determined once the inner diameter is decided from the preferred inner diameter-to-depth ratio. It should be noted, however, that the microchambers should preferably have a depth of 20 μm or more to contain cells. Taken together, it is particularly preferable that the microchambers in the microarray chip of the present invention have the foregoing ranges of inner diameter-to-depth ratio, the foregoing ranges of inner diameter, and a depth of 20 μm or more.

With these dimensions, the microchambers can evenly and efficiently contain cells in the form of a monolayer.

The microarray chip provided with such microchambers is suited for, for example, infected blood cells in an infection, particularly blood cells infected with malaria parasites. The microarray chip is also suited for various cultured cells (particularly, for example, mammal- or insect-derived cells, and yeasts).

The microarray chip of the present invention can evenly contain cells, for example, such as above, in the microchambers. Specifically, about the same number of cells can be contained in each microchamber. Thus, given that the number of microchambers in the microarray chip, and the number of cells contained in each microchamber are known, the number of cells retained by the microarray chip can be estimated. Once the number of detected specific cells is known, the percentage of the specific cells in the multiples cells contained in a sample can easily be calculated. Note that the method used to count the cells contained in the microchambers is not particularly limited. For example, the cells can be counted by observing the microchambers with a microscope.

The microarray chip of the present invention also can be suitably used for the screening of a drug candidate substance, as will be described later. Because each microchamber contains about the same number of cells, the state of the cells in each microchamber is uniform. This helps perform the comparative evaluation of the effects of different drug candidate substances on the cells after adding these substances to each microchamber.

Further, as described above, the microarray chip of the present invention can contain cells in the microchambers in the form of a monolayer. Specifically, the cells can be contained at the bottom of each microchamber with almost no overlap. Thus, detection problems caused when the target specific cell is underneath the overlying cells in the microchamber are unlikely to occur. Further, because the cells form a monolayer, a focal point can easily be set in microscopy.

Confocal laser microscope observation is also possible with high sensitivity, because of the suppressed background. Further, a different type of cells may be placed over the monolayer of cells, and the interaction between these cells can be efficiently studied. Further, the interaction between different cells can be studied in more detail by culturing the monolayer of cells with the cells placed on these cells.

Whether the cells are contained in the microchambers as a monolayer of cells can easily be confirmed by a skilled artisan by checking for overlapping cells through observation with a light microscope. Further, whether the cells are contained in the microchambers as a monolayer of cells without overlap can easily be confirmed, for example, by staining the cells with a dye (preferably, fluorescence dye) that stains the cell membrane, because such staining allows for easy checking of any overlapping cell membranes.

Further, the microarray chip of the present invention enables the cells to be cultured in the microchambers for at least several days. Generally, cultured cells tend to die out even in a suitable culture environment, for example, when the culture space is limited or when the cells are cultured in small numbers. However, the cells contained in the microchambers in the microarray chip of the present invention can be cultured for at least several days.

Thus, the target specific cell detected with the microarray chip of the present invention can be cultured in the microchambers. This enables time-dependent studies of the specific cell in the microchambers. For example, the specific cell may be cultured with stimuli to study the cell response. The stimuli are not particularly limited, and may be, for example, addition of chemicals such as growth factors and vitamins, changes in culture temperature, or addition of no essential nutrients. Stimuli that induce the specific cell to differentiate are preferable, because, in this case, the specific cell can be detected and induced to differentiate in the microchambers. Not being able to culture the cells in the microchambers is very inconvenient, because it requires culturing the cells in a petri dish with a differentiation-inducing stimulus, and then putting the cells back to the microchambers. Further, in case where the cells attach to the petri dish, the cell must be detached with the use of, for example, an enzyme, which might damage the cells and impair the cell functions.

Specifically, for example, after the detection of PC12 cells (Rat adrenal pheochromocytoma cell line) in the microchambers, the cells may be cultured for several days with addition of nerve growth factor (NGF) to induce differentiation into nerve-like cells and form a synaptic network.

In the screening of a drug candidate substance (described later), while some drug candidate substances show effects on the cells immediately after being added (within several minutes to several hours), other substances may take several days to show effects on the cells after the addition. Thus, the screening of a drug candidate substance may require observing the cell state after the cells are cultured and maintained several days following the addition of the drug candidate substance. In this regard, the microarray chip of the present invention can be suitably used for the screening of a drug candidate substance.

The microarray chip of the present invention can use a variety of cells as the detection target, as described above. For example, the microarray chip can target cultured cells, including blood cells, human-derived cells, animal cells, yeast cells, microorganism cells, stem cells, and cancer cells, as noted above. Further, with the use of the microarray chip of the present invention, only the target specific cell in the cells contained in a sample can be detected, measured, and analyzed, both rapidly and easily with high sensitivity.

(d) Screening of Drug Candidate Substance

The drug candidate substance screening method of the present invention can be used to easily and rapidly measure the effects various drug candidate substances on cells, and efficiently select a substance that exhibits desired activity.

The drug candidate substance screening method of the present invention uses a microarray chip that includes multiple microchambers and that retains cells in the microchambers.

In the drug candidate substance screening method of the present invention, a drug candidate substance is first added to the microchambers retaining the cells. The drug candidate substance added to the microchambers of the microarray chip may be the same or different. Preferably, the drug candidate substance is not added to some of the microchambers, and the cells retained in these microchambers are used as a control.

After adding the drug candidate substance, the effect of the drug candidate substance on the cells retained in the microchambers is measured. The method used to measure the effect of the drug candidate substance may be appropriately selected according to the types of drug candidate substance and cells used, and the desired activity.

For example, when screening for a substance that acts as an anticancer agent, cancer cells are retained in the microchambers, and the death rate and death time of the cancer cells after the addition of drug candidate substances are measured.

A substance that exhibits the desired activity can then be selected from the tested drug candidate substances, based on the measurement result. For example, when screening for a substance that acts as an anticancer agent, a substance that acted to kill the cancer cells at high rate may be selected.

In this way, large numbers of drug candidate substances can be screened both easily and rapidly.

The microarray chip used in the drug candidate substance screening method of the present invention is not particularly limited, and is preferably the microarray chip of the present invention. With the microarray chip of the present invention, the cells can be more evenly and efficiently contained in the microchambers in the form of a monolayer.

Further, with the microarray chip of the present invention, the cells can be cultured in the microchambers for at least several days, as described above. Thus, with the microarray chip of the present invention, the drug candidate substance screening method of the present invention can measure the effect of a drug candidate substance on the cells cultured and maintained for at least several days after the addition of the drug candidate substance.

Further, with the microarray chip of the present invention, because each microchamber contains about the same number of cells, the state of the cells in each microchamber can be made uniform. The drug candidate substance screening method of the present invention performed with the microarray chip of the present invention helps perform the comparative evaluation of the effects of different drug candidate substances on cells after adding these substances to each microchamber.

BRIEF DESCRIPTION OF DRAWINGS

FIG. 10 shows HEK-293 cells cultured in the microchambers of a microarray chip.

EXAMPLES

The present invention is described below based on Examples. The invention, however, is not limited by the following Examples.

Example 1

1. Microarray Chip used in Example 1

The following microarray chip was used in Example 1.
Microarray chip substrate: Polystyrene
Microarray chip surface treatment: Oxygen plasma process
Microchambers formed by: LIGA process
Number of cells per microchamber: About 100
Shape of microchamber: Cylindrical
Microchamber dimensions: Inner diameter, 100 μm; depth, 100 μm
Number of microchambers per microarray chip: 10,752
Distance between microchambers: 200 μm, corresponding to distance (i) in FIG. 1
Microarray chip surface water contact angle: 10°

Figure 3:
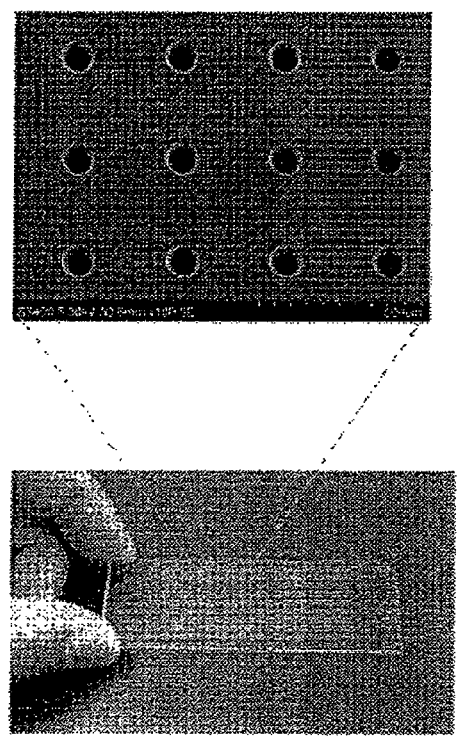
FIG. 3 is an illustration showing an example of a microarray chip used in Example 1, in which the microchambers of the microarray chip have an inner diameter of 100 μm, and a depth of 100 μm, and in which the shortest distance between the microchambers is 200 μm, and a total of 10,752 microchambers are provided.

FIG. 3 shows the microarray chip.

2. Fabrication Method of Microarray Chip Used in Example 1

The microarray chip was fabricated as follows.

In Example 1, a microarray chip (Starlite Co., Ltd.) fabricated by the LIGA process was used. Specifically, the microarray chip is the molded product obtained by flowing polystyrene in a nickel mold fabricated by the electroforming (plating) of a PMMA template obtained after the etching of a PMMA substrate patterned by X-ray lithography.

The surface of the microarray chip was rendered hydrophilic by an oxygen plasma process, which was performed at the output of 200 W for about 20 seconds using a reactive ion etching (RIE) apparatus (Samco).

The water contact angle of the hydrophilic microarray chip surface was measured according to the θ/2 method, as follows. Specifically, the water contact angle was measured at room temperature by dropping 1 to 2 μl of distilled water at different points (at least 5 points) on the microarray chip surface, using a contact angle meter (Kyowa Interface Science Co., Ltd.). The water contact angle was then determined from the mean value of the measured values.

The hydrophilic microarray chip was sonicated in advance to prevent entry of air into the microchambers and to thus make the development of the cell suspension on the microarray chip easier. The sonication was performed for about 5 minutes by immersing the surface-treated microarray chip in a medium (RPMI1640)-containing beaker, using a common ultrasonic washing apparatus.

3. Procedure for the Detection of Malaria Parasite-Infected Red Blood Cells (Fluorescence Labeling Method)

In Example 1, malaria parasite infection chosen used as the detection target, and the infected red blood cells were detected. The detection procedure by the fluorescence labeling method is as follows.

1) Malaria-infected red blood cells were obtained by culturing malaria parasites according to the malaria continuous culture method (W. Trager, J. B. Jensen, Science (1976) 673-675) under the following conditions: 37° C., 5% $CO_2$/5% $O_2$, 3% human red blood cells, 10% human serum-containing RPMI1640 medium. The malaria-infected red blood cells were then suspended in a culture solution (RPMI1640) at $1×10^8$ cells/ml to produce a suspension of malaria-infected red blood cells. Note that the human red blood cells were collected from a human individual, and used after centrifugation (4° C., 1500 g, 30 min).

From the result of cell counting under a microscope, the infection rate of the malaria parasites for the red blood cells was found to be 0.5%.

2) The malaria-infected red blood cells were stained by simultaneously adding two kinds of fluorescence dyes (DiI, SYTO59) to the suspension of malaria-infected red blood cells at the concentrations determined according to the recommended concentrations by the manufacturer. The cells were suspended, and fluorescence-stained by being incubated at 37° C. for 5 minutes.

3) 200 μl of the fluorescence-stained red blood cell suspension wad added to the microarray chip with a micropipette to contact and develop the red blood cells on the microarray chip.

4) The microarray chip was left unattended for 10 min at room temperature to allow the red blood cells to adsorb on the microarray chip.

5) The microarray chip surface was washed with a 1-ml culture solution (RPMI1640), using a micropipette.

6) After washing, the microarray chip was observed under a fluorescence microscope.

Figure 4:
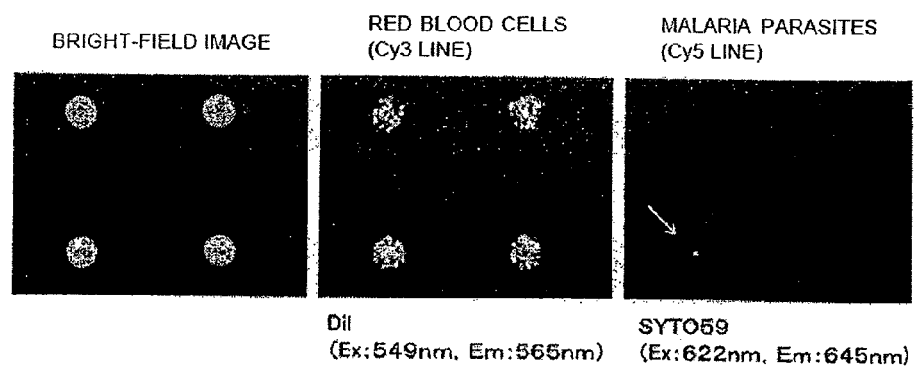
FIG. 4 represents the experiment results of Example 1.

The results are presented in FIG. 4. In FIG. 4, the photograph on the left is a bright-field image, showing the actual image in the vicinity of the bottom of the holes in the microarray chip. The photograph at the center of FIG. 4 shows all the red blood cells on the microarray chip after the staining of the cell membrane with DiI. The photograph on the right in FIG. 4 shows only the malaria parasite-infected red blood cells with the nuclei stained with SYTO59 (to be more precise, the fluorescence is due to the fluorescence-stained nuclei of the protozoa infecting the red blood cells).

About 100 red blood cells were successfully introduced into the 100 μm-diameter microchambers. The malaria parasite-infected red blood cells were successfully detected from the red blood cells contained in the microchambers.

It was found from these results that the detection method of the present invention could be sufficiently used for detection and diagnosis even when only about 0.0001% of all cells are infected.

4. Procedure for the Detection of Malaria Parasite-Infected Red Blood Cells (Giemsa Staining Method)

The procedure of detecting malaria parasite-infected red blood cells by a Giemsa staining method is as follows.

A certain number of red blood cells containing malaria parasite-infected red blood cells were retained in the microchambers of the microarray chip according to the method of Section 3 above, without fluorescence-staining the malaria-infected red blood cells.

The remaining water on the cell chip surface was removed with a glass slide and a cell scraper. Then, the cells were dried and fixed by quickly removing the water in the microchambers at a temperature (room temperature to 60° C.) that does not burst the cells, using a vacuum pump and a dryer. The whole microarray chip was then immersed in 100% methanol (room temperature, 30 min) for methanol fixation. This was followed by staining, which was performed by immersing the whole microarray chip in a Giemsa stain solution (Merck) at room temperature for 30 min.

After the staining, the procedure of washing the microarray chip by immersing the whole chip in distilled water was repeated three times, and the microchambers were dried by quickly removing water in the microchambers at a temperature (room temperature to 60° C.) that does not burst the cells, using a vacuum pump and a dryer. The cells were then observed with a light microscope.

Figure 5:
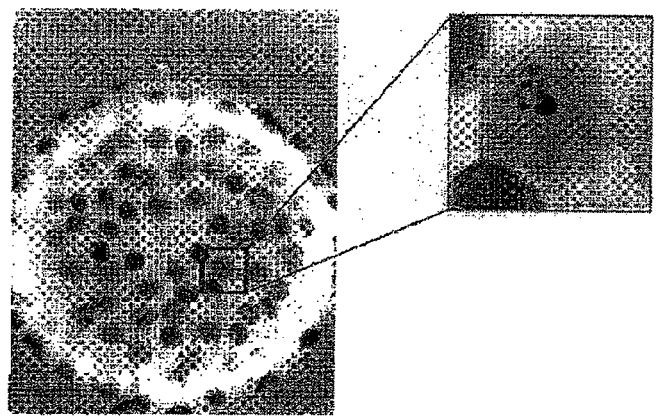
FIG. 5 shows red blood cells infected with a malaria parasite, and detected by Giemsa staining in the microchambers of a microarray chip.

The results are presented in FIG. 5. As shown in FIG. 5, Giemsa staining and detection of the malaria parasites were possible in the microchambers of the microarray chip.

Example 2

Water contact angle and cell development efficiency were compared, as follows.

1. Fabrication of Microarray Chip

Three kinds of microarray chips with different water contact angles (water contact angles of 80°, 25°, and 10°) were fabricated. These microarray chips were fabricated in the same manner as described in Example 1, under different oxygen plasma process conditions to provide different water contact angles. Specifically, the oxygen plasma process was performed under the following conditions.

Microarray Chip with a Water Contact Angle of 80°:
  Surface treatment was performed at an output of 200 W for 3 seconds using a RIE apparatus (Samco).
Microarray Chip with a Water Contact Angle of 25°:
  Surface treatment was performed at an output of 200 W for 5 seconds using a RIE apparatus.
Microarray Chip with a Water Contact Angle of 10°:
  Surface treatment was performed at an output of 200 W for 20 seconds using a RIE apparatus.

2. Detection Procedure of Red Blood Cells

In Example 2, red blood cells uninfected with malaria parasites were used. Specifically, red blood cells were detected, and the cells were compared with regard to development efficiency, as follows.

First, the red blood cells collected from a human individual and centrifuged as in Example 1 were suspended in a medium (RPMI1640) to obtain a suspension of human-derived red blood cells (the concentration of red blood cells in the suspension: $1 \times 10^8$ cells/ml). 200 µl of the red blood cell suspension was added to a microarray chip as in Example 1 to contact and develop the red blood cells on the microarray chip, and the number of microchambers that contained the red blood cells was confirmed with a microscope. Note that because the red blood cells appear pale red in color under a microscope, the presence or absence of the red blood cells in the microchambers can be determined by the color inside the microchambers (the color of the red blood cells). Specifically, the microchambers can be determined as containing the red blood cells when the microchambers appear pale red in color, and not containing the red blood cells when the microchambers are not pale red. Accordingly, fluorescence staining was not performed in Example 2 and in Example 4 below.

3. Results

Figure 6:
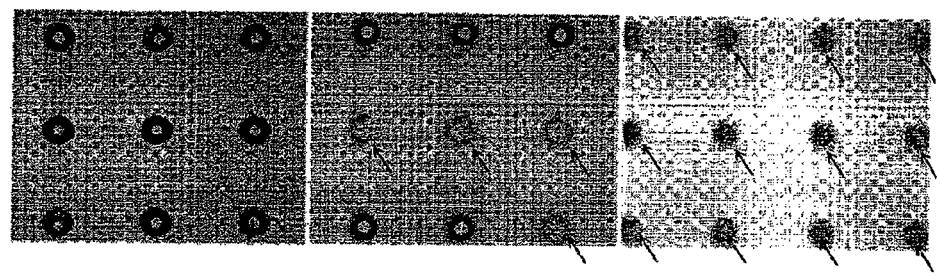
FIG. 6 represents differences in cell development rate at different water contact angles; left, essentially all cells fail to enter the chambers of the microarray chip (water contact angle, 80°; cell development rate, 10% or less); center, cells fail to enter some of the chambers of the microarray chip (surface water contact angle, 25°; cell development rate, about 40%); right, the cells are evenly present in almost all chambers of the microarray chip (water contact angle, 10°; cell development rate, 90% or more).

The results are presented in FIG. 6. As used herein, the "cell development efficiency" means the proportion of cell-containing microchambers in the total number of microchambers provided in the microarray chip.

Hardly any cell entered the microchambers when the water contact angle of the microarray chip was 80°, whereas the cells were contained in about 40% of the microchambers at the water contact angle of 25°. At the 10° water contact angle, the cells were contained in 90% or more of the microchambers.

Example 3

1. Fabrication of Microarray Chip

Microarray chips with water contact angles of 80° or more and 10° or less were fabricated in the same manner as in Example 2.

2. Detection Procedure of Red Blood Cells

As in Example 2, red blood cells not infected with malaria parasites were used, and the development efficiency of the cells in each microarray chip was compared.

3. Results

Hardly any cell entered the microarray chip when the water contact angle was 80° or more, whereas the cells were contained in 90% or more of the microchambers at the water contact angle of 10° or less. For example, the cells were desirably contained in the microchambers when the water contact angle was 5° or less.

Example 4

Assessment of the Red Blood Cell Retaining Ability of Microchambers

The cells contained in the microchambers were studied with regard to changes that occurred with changes in the inner diameter and depth of the microchambers in a microarray chip.

Production of Microarray Chip

Three kinds of microarray chips provided with cylindrical microchambers of the inner diameters and depths below were produced (microarray chips A to C).

Microarray Chip A:
  Inner diameter: 105 µm
  Depth: 50 µm
  Inner diameter:depth≈1:0.48
Microarray Chip B:
  Inner diameter: 500 µm
  Depth: 150 µm
  Inner diameter:depth=1:0.3
Microarray Chip C:
  Inner diameter: 50 µm
  Depth: 40 µm
  Inner diameter:depth=1:0.8

Figure 1:
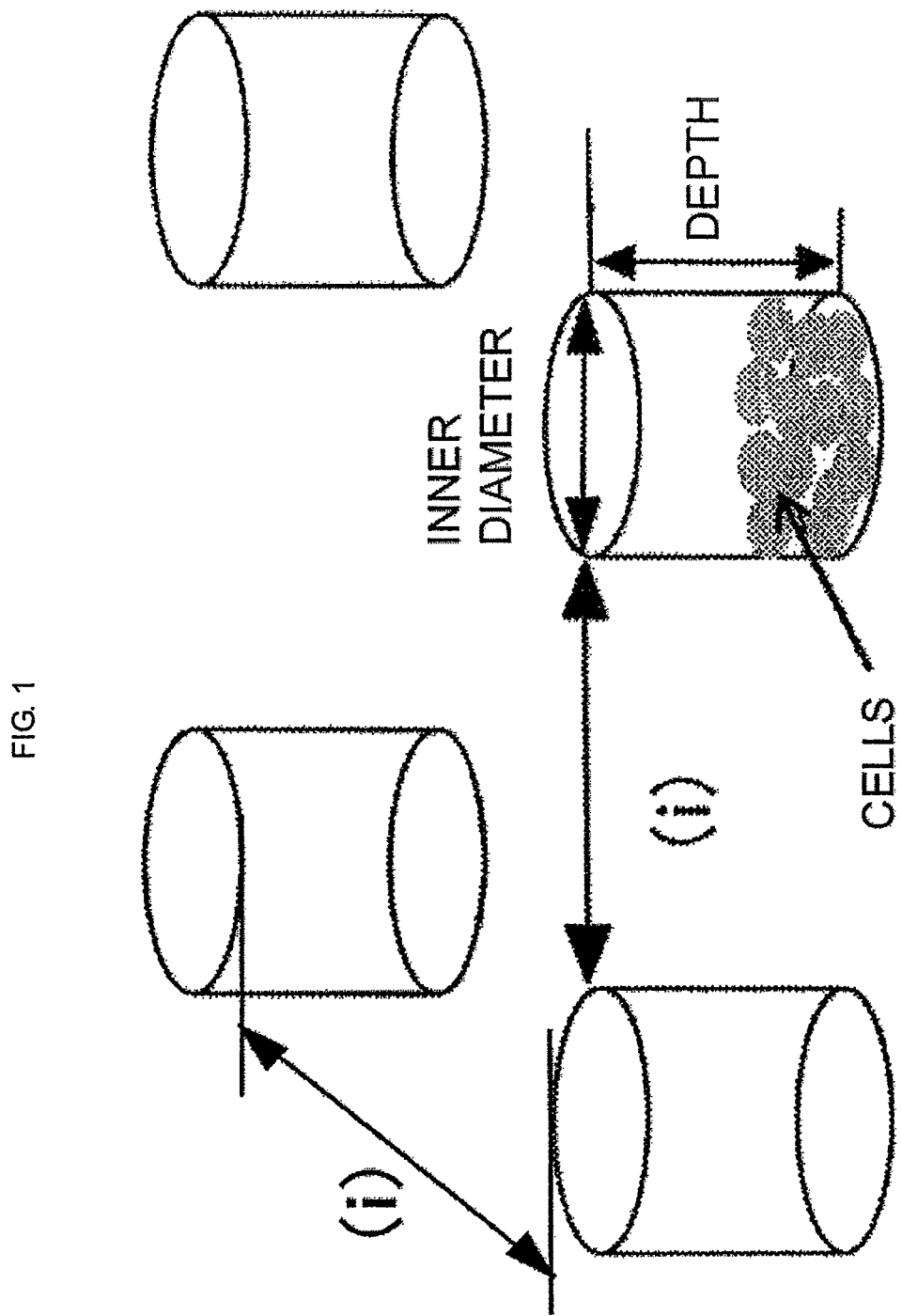
FIG. 1 is an illustration showing distance (i) between microchambers disposed in a grid.
Figure 2:
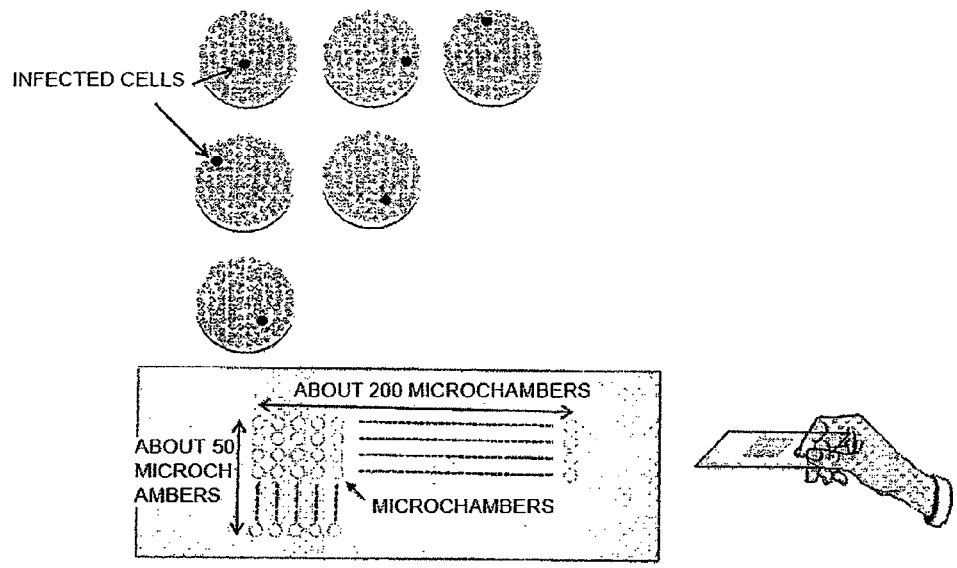
FIG. 2 is an illustration representing an example in which a single infected blood cell is detected per microchamber in a microarray chip containing 100 blood cells in each of the 50×200 microchambers disposed along the columns and rows of the chip.

The microarray chips A to C are the same as the microarray chip produced in Example 1, except for the inner diameter, the depth, the distance between the microchambers (the distance corresponding to distance (i) in FIG. 1), and the number of contained cells, and were produced according to the method of Example 1. The distances between the microchambers are as follows.

Microarray chip A: 200 μm
Microarray chip B: 500 μm
Microarray chip C: 200 μm

Development of Red Blood Cells on Microarray Chip

The red blood cells collected from a human individual and centrifuged as in Example 1 were suspended in a medium (RPMI1640) to obtain a suspension of human-derived red blood cells (the concentration of red blood cells in the suspension: $5.0 \times 10^7$ cells/ml). 200 μl of the red blood cell suspension was added to a microarray chip as in Example 1 to contact and develop the red blood cells on the microarray chip, and the number of microchambers that contained the red blood cells was confirmed with a microscope.

Figure 7:
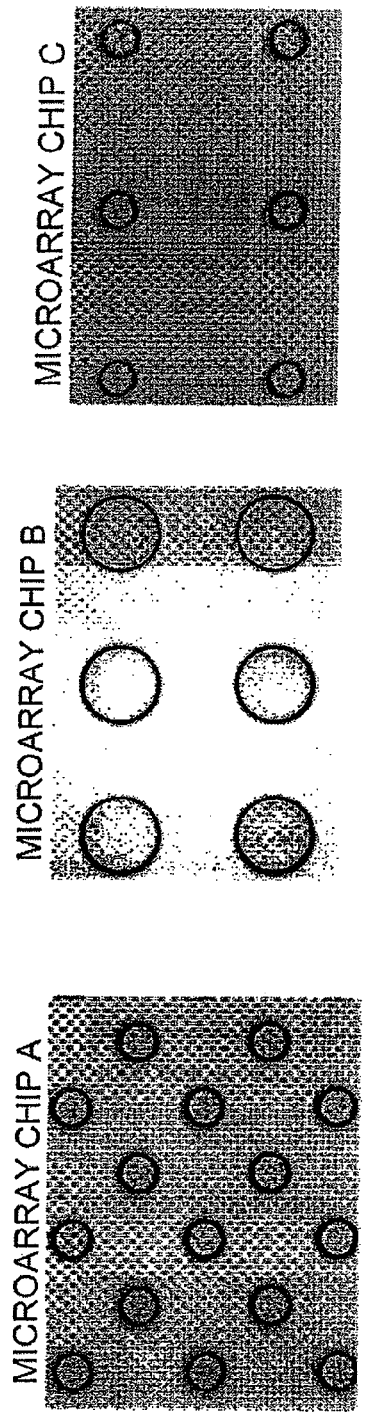
FIG. 7 shows red blood cells contained in the microchambers of three kinds of microarray chips that include microchambers of different inner diameters and different depths.

The results are presented in FIG. 7. As shown in FIG. 7, the cells observed under a microscope were contained in each microchamber without overlap in the microarray chips A and C. Further, as a result of counting the cells under a microscope, it was found that about the same number of cells were contained in each microchamber. It was therefore found that the red blood cells were evenly retained as a monolayer of cells at the bottom of each microchamber. In microarray chip B, some microchambers had large unbound areas on their bottom surfaces where the red blood cells were not attached. This was considered to be due to the washing of the red blood cells attached to the bottom of the microchambers during the washing of the microarray chip. It was therefore considered difficult to evenly retain the cells as a monolayer in microchambers having an inner diameter as large as about 500 μm, when the depth is 150 μm or less. Further, because the red blood cells were evenly retained as a monolayer at the bottom of each microchamber in microarray chips A and C, the preferred inner diameter-to-depth ratio of the microchambers was considered to be about 1:0.35 to 1.

Example 5

Development of Various Cells on Microarray Chip

Assessment was made as to the retention of HEK-293 cells (hereinafter, "HEK cells") and yeasts in the microchambers, using the microarray chips A and C produced in Example 4.

HEK Cells

HEK cells were cultured in DMEM/10% FBS medium according to an ordinary method. The cells were collected, and suspended in the same medium at $1 \times 10^5$ cells/ml. 200 μl of the suspension was added to the microarray chip C with a micropipette to contact and develop the HEK cells on the microarray chip C. The surface of the microarray chip C was then washed with 1 ml of the culture solution using a micropipette, and the bright-field image was observed with a light microscope. The results are presented in FIG. 8.

Yeasts

Two hundred milliliters of a suspension of yeasts in a medium (YPN; basal medium; cell concentration, $3.6 \times 10^8$ cells/ml) was developed on microarray chip A using a Pipetman. The chip was allowed to stand for 20 min, and the chip surface was washed with medium or the like. The bright-field image was then observed with a light microscope. The results are presented in FIG. 9.

Figure 8:
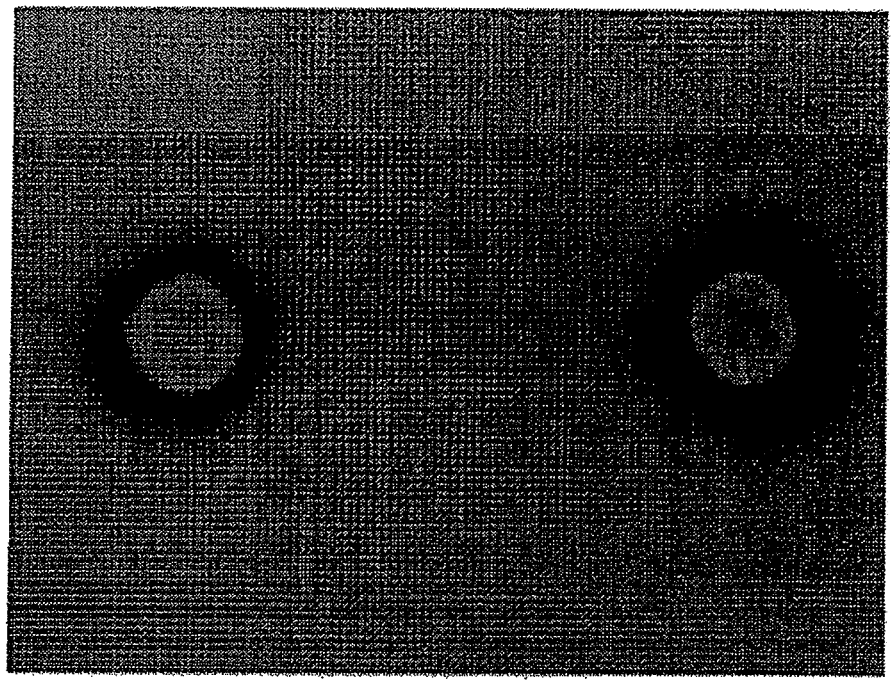
FIG. 8 shows HEK-293 cells retained in the microchambers of a microarray chip.
Figure 9:
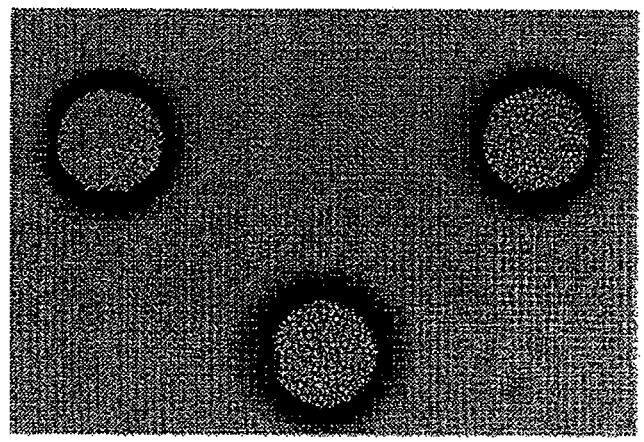
FIG. 9 shows yeasts retained in the microchambers of a microarray chip.

As shown in FIGS. 8 and 9, the HEK cells and the yeasts were contained in each microchamber without overlap. It was found from this that the HEK cells and the yeasts were evenly retained as a monolayer of cells in each microchamber. From this result, the microchambers in the microarray chip of the present invention were found to be capable of evenly retaining various types of cells as a monolayer.

Example 6

Cell Culture in Microchambers

Whether cells can be cultured in the microchambers was examined by culturing the HEK cells with the microarray chip C produced in Example 4.

Specifically, the cells were cultured as follows. The HEK cells ($1 \times 10^6$ cells/ml) were developed on the microarray chip C, and washed according to the method of Example 5. The whole microarray chip C was immersed in a culture liquid medium (DMEM/10% FBS medium), and cultured in a $CO_2$ incubator (5% $CO_2$ concentration, 37° C.). In the $CO_2$ incubator, the medium used to immerse the microarray chip was replaced with a new medium every 24 hours. When replacing the medium, the chip surface was washed also with a new medium to ensure that the medium inside the microchambers was also replaced.

The results are presented in FIG. 10. The number of HEK cells increased after 4 days of culturing from that immediately after the cells were developed on the microarray chip C and retained in the microchambers. This, combined with the presence of cells that underwent morphological changes, confirmed that the HEK cells were successfully cultured.

The invention claimed is:

1. A method for detecting a specific cell in a sample containing multiple cells,
    the method comprising the steps of:
    (1) retaining sample cells in a microarray chip provided with multiple microchambers and capable of containing multiple cells in each microchamber,
    wherein the microarray chip has a surface that has a water contact angle of 10° or less and the surface of the microarray chip includes the inner surface of the microchambers,
    and wherein the microchambers have an inner diameter-to-depth ratio of 1:0.35 to 0.85 and an inner diameter of from 20 to 500 μm, sample cells are capable of forming a monolayer at the bottom of each microchamber, and the microchamber can contain at least two cells; and
    (2) detecting a labeled specific cell in the cells retained in the microarray chip, wherein the labeled specific cell is labeled after the step (1), or the labeled specific cell is labeled prior to the step (1).

2. A detection method according to claim 1, wherein the microchambers have a depth of 20 μm or more.

3. A detection method according to claim 1, wherein the specific cell is a cell infected with an infection causative agent.

4. A detection method according to claim 3, wherein the infection causative agent is a malaria parasite.

5. A detection method according to claim 1, wherein the sample containing multiple cells is a sample containing multiple blood cells.

6. A detection method according to claim 1, the labeled specific cell is labeled with a label capable of fluorescence.

7. A detection method according to claim 1, wherein the microchambers are disposed in a grid and the shortest distance between the microchambers is at least 100 to at most 200 μm.

8. A detection kit for detecting a specific cell in a sample containing multiple cells, the detection kit comprising a microarray chip provided with multiple microchambers, and that is capable of containing multiple cells in each microchamber, wherein the microarray chip has a surface that has a water contact angle of 10° or less and the surface of the microarray chip includes the inner surface of the microchambers, and wherein the microchambers have an inner diameter-to-depth ratio of 1:0.35 to 0.85 and an inner diameter of from 20 to 500 μm, sample cells are capable of forming a monolayer at the bottom of each microchamber, and the microchambers can contain at least two cells.

9. A detection kit according to claim 8, wherein the sample containing multiple cells is a sample containing multiple blood cells, and wherein the specific cell is a blood cell infected with an infection causative agent.

10. A detection kit according to claim 8, wherein the microchambers are disposed in a grid and the shortest distance between the microchambers is at least 100 to at most 200 μm.

11. A detection kit according to claim 8, wherein the microchambers have a depth of 20 μm or more.

12. A microarray chip that comprises multiple microchambers, wherein the microarray chip is capable of containing multiple cells in each microchamber, and has a surface that has a water contact angle of 10° or less, wherein the surface of the microarray chip includes the inner surface of the microchambers, and wherein the microchambers have an inner diameter-to-depth ratio of 1:0.35 to 0.85 and an inner diameter of from 20 to 500 μm, sample cells are capable of forming a monolayer at the bottom of each microchamber, and the microchambers can contact at least two cells.

13. A microarray chip according to claim 12, wherein the microchambers have a depth of 20 μm or more.

14. A microarray chip according to claim 12, wherein cells are contained in the microchambers.

15. A microarray chip according to claim 12, wherein the microchambers are disposed in a grid and the shortest distance between the microchambers is at least 100 to at most 200 μm.

* * * * *